US011191714B2

(12) United States Patent
Li et al.

(10) Patent No.: US 11,191,714 B2
(45) Date of Patent: Dec. 7, 2021

(54) ROBUST SUNSCREEN COMPOSITIONS

(71) Applicant: Edgewell Personal Care Brands, LLC, Chesterfield, MO (US)

(72) Inventors: Geng Li, Rutherford, NJ (US); James SaNogueira, Wesley Hills, NY (US)

(73) Assignee: EDGEWELL PERSONAL CARE BRANDS, LLC, Chesterfield, MO (US)

(*) Notice: Subject to any disclaimer, the term of this patent is extended or adjusted under 35 U.S.C. 154(b) by 0 days.

(21) Appl. No.: 16/786,365

(22) Filed: Feb. 10, 2020

(65) Prior Publication Data

US 2020/0170921 A1 Jun. 4, 2020

Related U.S. Application Data

(63) Continuation of application No. 15/560,680, filed as application No. PCT/US2016/019533 on Feb. 25, 2016, now Pat. No. 10,617,627.

(60) Provisional application No. 62/121,029, filed on Feb. 26, 2015.

(51) Int. Cl.
| | |
|---|---|
| *A61K 8/86* | (2006.01) |
| *A61Q 17/04* | (2006.01) |
| *A61K 8/81* | (2006.01) |
| *A61K 8/87* | (2006.01) |
| *A61K 8/88* | (2006.01) |
| *A61K 8/90* | (2006.01) |
| *A61K 8/35* | (2006.01) |
| *A61K 8/37* | (2006.01) |
| *A61K 8/40* | (2006.01) |
| *A61K 8/85* | (2006.01) |

(52) U.S. Cl.
CPC ............... *A61K 8/86* (2013.01); *A61K 8/35* (2013.01); *A61K 8/37* (2013.01); *A61K 8/40* (2013.01); *A61K 8/8111* (2013.01); *A61K 8/8117* (2013.01); *A61K 8/8141* (2013.01); *A61K 8/8147* (2013.01); *A61K 8/8152* (2013.01); *A61K 8/8182* (2013.01); *A61K 8/85* (2013.01); *A61K 8/87* (2013.01); *A61K 8/88* (2013.01); *A61K 8/90* (2013.01); *A61Q 17/04* (2013.01); *A61K 2800/40* (2013.01); *A61K 2800/54* (2013.01); *A61K 2800/594* (2013.01); *A61K 2800/5922* (2013.01)

(58) Field of Classification Search
CPC ........ A61K 2800/5922; A61K 2800/40; A61Q 17/04
See application file for complete search history.

(56) References Cited

U.S. PATENT DOCUMENTS

| | | |
|---|---|---|
| 2011/0104078 A1 | 5/2011 | Burgo et al. |
| 2012/0244097 A1* | 9/2012 | Lu ............................ A61K 9/06 |
| | | 424/64 |
| 2014/0170192 A1 | 6/2014 | Halpern et al. |

FOREIGN PATENT DOCUMENTS

| | | | |
|---|---|---|---|
| CN | 103249395 A | 8/2013 | |
| EP | 0955995 A1 | 11/1999 | |
| EP | 1521795 A2 | 4/2005 | |
| EP | 0955995 B1 * | 5/2006 | ............... A61K 8/36 |
| EP | 1700825 A1 | 9/2006 | |
| WO | 00/18367 A1 | 4/2000 | |
| WO | 2015/139782 A1 | 9/2015 | |

OTHER PUBLICATIONS

"Thermogelling properties of purified poloxamer 407", Heliyon 3 (2017) e00390 (Year: 2017).*
IP Australia, "Examination report No. 1 for standard patent applications", dated Jun. 16, 2020 for corresponding AU Application No. 2016222629.
Ubifrance, in Cosmetics Hambourg Apr. 1-3, 2014 [retrieved from internet on Jun. 9, 2020], <URL: https://www.youbuyfrance.com/medias/document/katalog-in-cosmetics-hamurg-2014_7_3_2014_48_30.pdf>.
Unofficial translation of Second Chinese Office Action issued in connection with Chinese Application No. 201680012693.3 dated Jun. 12, 2020.
Ken Klein: "Formulating Water-Resistant Sunscreen Emulsions", Cosmetics & Toiletries, Wheaton, IL, US, Feb. 1, 2002 (Feb. 1, 2002), pp. 1-3, XP0080797 45, ISSN: 0361-4387.
Kobo Products Inc: "Waterproof Suncare Lotion", Internet Citation, Oct. 2003, p. 1, XP002691962, Retrieved from the Internet: URL:http://www.koboproductsinc.com/formulations/KSL-089.pdf [retrieved on Feb. 11, 2012].
EPO Examination Report issued in connection with corresponding EP Application No. 16708899.6 dated Nov. 27, 2018.
"Suncare compositions with new cosmetic raw material (6)", ip.com Journal, ip.com Inc., West Henrietta, NY, US, Dec. 15, 2015, XP013168810, ISSN: 1533-0001.
International Search Report and Written Opinion issued in connection with corresponding PCT Application No. PCT/US2016/019533 dated May 23, 2016.
International Preliminary Report on Patentability issued in connection with corresponding PCT Application No. PCT/US2016/019533 dated Aug. 29, 2017.
Unofficial translation of Chinese Search Report issued in connection with corresponding CN Application No. 201680012693.3 dated Feb. 18, 2020.
Unofficial translation of Chinese Office Action issued in connection with corresponding CN Application No. 201680012693.3 dated Feb. 26, 2020.

* cited by examiner

Primary Examiner — James W Rogers

(57) ABSTRACT

A robust sunscreen composition is disclosed herein comprising a water soluble polymer and a water insoluble film former providing a synergistic effect in SPF retention and critical wavelength after immersion in water, salt water, and chlorinated water. The water soluble polymer comprises poloxamer 338 (and) PPG-12/SMDI copolymer, poloxamer 407 (and) PPG-12/SMDI copolymer, or a combination thereof.

16 Claims, No Drawings

ROBUST SUNSCREEN COMPOSITIONS

CROSS-REFERENCE TO RELATED APPLICATIONS

This application is a continuation of the U.S. patent application Ser. No. 15/560,680, filed Sep. 22, 2017, which is the National Phase of International Application No. PCT/US2016/019533, filed Feb. 25, 2016, claiming priority to U.S. Provisional Patent Application Ser. No. 62/121,029, filed Feb. 26, 2015, the contents of which are hereby incorporated by reference in their entirety.

BACKGROUND OF THE INVENTION

A. Field of Endeavor

The present disclosure relates to sunscreen compositions that have improved water resistance.

B. Background Information

Sun protection products have evolved considerably from the white titanium oxide stripe on a life guard's nose to advanced organic sunscreen compositions that provide broad spectrum protection from ultraviolet (UV) radiation in the UVA region (320 to 400 nm) and UVB region (290 to 320 nm). Protection from UVA radiation is measured as a Protection Factor—UVA or PFA. Protection from UVB radiation is measured as a Sun Protection Factor or SPF.

Active consumers today not only seek broad spectrum sun protection, but they also want water resistance while enjoying water activities. Sunscreen manufacturers provide the consumer with a water resistance rating that is dictated by the 2011 U.S. Food & Drug Administration (FDA) final monograph for water resistance wherein a sunscreen composition must meet the critical wavelength of 370 nm after water immersion for 40 minutes for a rating of water resistant (WR) or 80 minutes for a rating of very water resistant (VWR). However, the critical wavelength protocol does not take into account the efficacy of the sunscreen composition after exposure to real life conditions of heat, sweat, salt water or chlorinated pool water. Under these conditions of heat, salt, and/or chemicals, the sunscreen composition can lose its efficacy and provide limited or no protection to the consumer. Furthermore, when the sunscreen composition is exposed to excessive heat, for example, when it is stored in a hot car, the sunscreen product will thin out and become difficult to apply. The heat may also affect the efficacy of the sunscreen actives as well.

United States Patent Application No. 2011/0269839 is directed to a water soluble thermo gelling polymer for treating and/or preventing snoring that is a liquid in the packaging, but upon contact with mucus membranes at 37° C., becomes a gel. While the thermo gelling makes it possible to target a treatment area within the body, it is unclear whether the thermo gelling polymer will withstand adverse conditions of continuous contact with water, in particular, salt or pool water.

United States Patent Application No. 2014/0170192 discloses a sunscreen composition that includes at least one UV filter, at least one booster, at least one thermo sensitive polymer, and at least one wetting agent. The sunscreen compositions exhibit a high SPF mainly due to the use of very specific ratios of sunscreen actives in combination with a SPF booster such as, SUNSPHERES® glass microspheres. However, since both the thermo sensitive polymer and wetting agent are both highly water soluble, they will contribute little in the way of water resistance.

U.S. Pat. No. 7,339,013 is directed to a thermo sensitive polymer and its synthesis. Aqueous solutions of the polymers can be applied at low viscosity to the body. The polymers then gellify with an increase in temperature such as when applied to human skin. However, there is no suggestion given its water solubility that when incorporated into a sunscreen composition, the polymers would provide enhanced water resistance under adverse conditions that include sweat and/or chlorine.

Thus, there is a need to provide a more robust sunscreen formulation that preserves the efficacy and water resistance of the sunscreen composition after exposure to heat, sweat, salt water, and other adverse conditions.

SUMMARY

The present disclosure is directed, in a first aspect, to a sunscreen composition comprising one or more sunscreen actives; a water soluble polymer having a solubility of at least 10 wt. % in an aqueous solution at 25° C.; and a water insoluble polymer, wherein a combination of said water soluble polymer and said water insoluble polymer preserves at least one of in vitro SPF effectiveness and critical wavelength after exposure to water and salt.

The one or more sunscreen actives comprises p-aminobenzoic acid and derivatives thereof; butyl methoxydibenzoylmethane; benzophenones; hydroxy-substituted benzophenones; methoxy-substituted benzophenones; benzophonone-1; benzophenone-2; benzophenone-3; benzophenone-4; benzophenone-6; benzophenone-8; benzophenone-12; methoxycinnamate; ethyl dihydroxypropyl-p-aminobenzoate; glyceryl-p-aminobenzoate; homosalate; methyl anthranilate; octocrylene; octyl dimethyl-p-aminobenzoate; octyl methoxycinnamate; octyl salicylate; 2 phenylbenzimidazole-5-sulphonic acid; triethanolamine salicylate; 3-(4-methylbenzylidene)-camphor; red petrolatum, 3-(4-methylbenzyldine)boran-2-one(methylbenzindinecamphor); benzotriazole; salicylates; phenylbenzimidazole-5-sulfonic acid; methylene bis-benzotriazolyl tetramethylbutyl phenol; avobenzone; 4-isopropyldibenzoylmethane; butyl-methoxydibenzoylmethane; octisalate; oxybenzone; bis-ethylhexyloxyphenol methoxy triazine; 4-isopropyl-dibenzoylmethane; metal oxides; zinc oxide; octyltriethoxy silanol; titanium dioxide; alumina; and triethoxy silane.

The water soluble polymer may be present in an amount of about 0.01 wt. % to about 10 wt. %. Preferably, the water soluble polymer is poloxamer 338 (and) PPG-12/SMDI copolymer, poloxamer 407 (and) PPG-12/SMDI copolymer, or a combination thereof.

The water insoluble polymer may comprise of acrylate copolymers, methacrylate copolymers, styrene copolymers, stearate copolymers polyamide copolymers, polyvinylpyrrolidone copolymers, polyurethane copolymers, polyester copolymers, polyolefin copolymers, or combinations thereof. Preferably, the water insoluble polymer is present in an amount of about 0.01 wt. % to about 5.0 wt. %.

In preferred embodiments, the combination of the water soluble polymer and the water insoluble polymer preserves an in vitro SPF effectiveness of at least 70% after exposure to salt water. Preferably, the combination of the water soluble polymer and the water insoluble polymer retains an in vitro SPF effectiveness of at least 85% after exposure to salt water. In some embodiments, the combination of said water soluble polymer and said water insoluble polymer retains a critical wavelength of at least 370 nm after exposure to water and/or salt water.

In another aspect, the present invention is directed to a sunscreen composition comprising a photoprotective agent comprising one or more of homosalate, octisalate, octocrylene, or avobenzone; a water soluble polymer comprising poloxamer 338 (and) PPG-12/SMDI copolymer; and a water insoluble polymer.

Preferably, the water soluble polymer further comprises poloxamer 407 (and) PPG-12/SMDI copolymer, and is present in an amount of 1.0 wt. % to 10 wt. %, or more preferably, in an amount of 1.5 wt. % to about 5.0 wt. %.

Preferably, the water insoluble polymer comprises acrylate copolymers, methacrylate copolymers, styrene copolymers, stearate copolymers polyamide copolymers, polyvinylpyrrolidone copolymers, polyurethane copolymers, polyester copolymers, polyolefin copolymers, or combinations thereof. More preferably, the water insoluble polymer comprises acrylate copolymers, styrene copolymers, stearate copolymers, polyamide copolymers, or combinations thereof. The water insoluble polymer may be present in an amount of about 0.1 wt. % to 2.5 wt. %.

In yet another aspect, the present invention is directed to a consumer packaged product comprising a sunscreen composition comprising one or more sunscreen actives; a water soluble polymer having a solubility of at least 10 wt. % in an aqueous solution at 25° C.; and a water insoluble polymer, wherein a combination of said water soluble polymer and said water insoluble polymer preserves at least one of in vitro SPF effectiveness and critical wavelength after exposure to water and salt water.

In yet another aspect, the present invention is directed to a consumer packaged product comprising a sunscreen composition comprising a photoprotective agent comprising one or more of homosalate, octisalate, octocrylene, or avobenzone; a water soluble polymer comprising poloxamer 338 (and) PPG-12/SMDI copolymer; and a water insoluble polymer.

Also disclosed are methods of treating a keratinous substrate such as hair or skin using the sunscreen compositions of the present invention.

DETAILED DESCRIPTION OF THE INVENTION

The embodiments of the present disclosure can comprise, consist of, and consist essentially of the features and/or steps described herein, as well as any of the additional or optional ingredients, components, steps, or limitations described herein or would otherwise be appreciated by one of skill in the art. It is to be understood that all concentrations disclosed herein are by weight percent (wt. %.) based on a total weight of the composition unless otherwise indicated.

The present disclosure is directed to a sunscreen composition that preserves the integrity of the sunscreen even after exposure to adverse conditions such as heat, sweat, and salt water. The sunscreen composition comprises of one or more sunscreen actives, a water soluble polymer, and a water insoluble polymer, wherein the combination of the water soluble polymer and the water insoluble polymer preserves at least one of in vitro SPF effectiveness and critical wavelength after exposure to heat and sweat. It is unexpected that a water soluble component in the sunscreen composition can provide an improvement in water resistance of the final sunscreen composition. Also, this combination provides a heat responsive sunscreen composition wherein the response is triggered at a skin temperature of about 30° C. or higher such that at or above the trigger temperature, the sunscreen increases in viscosity to provide a consumer noticeable film formation for added sun protection and water resistance.

The one or more sunscreen actives that can be used in the present invention must be capable of absorbing or blocking the harmful effects of ultraviolet radiation to provide broad spectrum protection. In addition, they must be non-toxic and non-irritating when applied to the skin. Suitable sunscreen actives that may be used in the sunscreen composition include, but are not limited to, one or more of the following: p-aminobenzoic acid and derivatives thereof; butyl methoxydibenzoylmethane; 2,4-dihydroxybenzophenone; 2,2',4,4'-tetrahydroxybenzophenone; oxybenzone; sulisobenzone; sulisobenzone sodium; 2,2'-dihydroxy-4,4'-dimethoxybenzophenone; 5-chloro-2-hydroxybenzophenone; dioxybenzone; sodium 2,2'-dihydroxy-4,4'-dimethoxybenzophenone-5,5'-disulfonate; 2-hydroxy-4-methoxy-4'-methyl-benzophenone; octabenzone; ethyl dihydroxypropyl-p-aminobenzoate; glyceryl-p-aminobenzoate; homosalate; methyl anthranilate; octocrylene; octyl dimethyl-p-aminobenzoate; isoamyl-p-methoxycinnamate; octyl methoxycinnamate; octyl salicylate; triethanolamine salicylate; 3-(4-methylbenzylidene) camphor; enzacamene; red petrolatum; phenylbenzimidazole sulfonic acid; methylene bis-benzotriazolyl tetramethylbutyl phenol; 4-isopropyldibenzoylmethane; butylmethoxydibenzoylmethane; octisalate; bis-ethylhexyloxyphenol methoxyphenyl triazine; 4-isopropyl-dibenzoylmethane; metal oxides; zinc oxide; titanium dioxide; alumina; terephthalylidene dicamphor sulfonic acid; drometrizole trisiloxane; diethylhexylbutamido triazone; octyltriazone; cinoxate; ensulizole; bis-disulizole disodium; diethylaminohydroxybenzoylhexylbenzoate; and combinations thereof. Preferred sunscreen actives that provide broad spectrum protection are homosalate, octisalate, octocrylene, oxybenzone, avobenzone, or combinations thereof.

The one or more sunscreen actives are present in an amount of about 1.0 wt. % to about 40.0 wt. %, based on a total weight of the sunscreen composition. The amount and types of photoactives in the composition will vary in the above range depending on the sun protection factor (SPF) desired. The higher the SPF, the greater the total amount of photoactives. Preferably, the one or more sunscreen actives are present in an amount of about 3.0 wt. % to about 30.0 wt. % to achieve a SPF of about 80 to about 200 and more, based on a total weight of the sunscreen composition. More preferably, the one or more additional sunscreen agents are present in an amount of about 3.0 wt. % to about 25.0 wt. %, based on a total weight of the sunscreen composition.

The water soluble polymer essential in the inventive sunscreen composition does not, by itself, provide any SPF nor does it act as a water proofer, yet it surprisingly maintains the SPF of the sunscreen composition after exposure to adverse conditions such as water, salt, AND chlorine. Preferably, the water soluble polymer has a water solubility of at least about 10 wt. % in an aqueous solution at 25° C. More preferably, the water soluble polymer has a water solubility of at least about 15 wt. %, and even more preferably, a water solubility of at least 20 wt. % in an aqueous solution at 25° C. The water soluble polymer is present in the invention sunscreen composition in an amount of about 0.01 wt. % to about 20 wt. %, more preferably in an amount of about 0.01 wt. % to about 10 wt. %, and most preferably in an amount of about 0.01 wt. % to about 5 wt. %, and may even be 0.01 wt. % to about 2 wt. %., based on a total weight of the sunscreen composition. Upon contact with the skin having a temperature of about 30° C. or under hot conditions, the inventive sunscreen composition provides a consumer perceived sensation of firming up on the skin to provide a barrier for protection.

Preferably, the water soluble polymer comprises triblock polymers, also known as poloxamers, of polyethylene oxide (PEO) and polypropyleneoxide (PPO), and mixtures thereof. Commercially available water soluble polymers are Poloxamer 338 (and) Polypropyleneglycol-12(PPG-12)/saturated methylenediphenyldiisocyanate (SMDI) copolymer; and Poloxamer 407 (and) PPG-12/SMDI copolymer. The water soluble polymers may be used alone or in combination. These water soluble polymers may be available from PolymerExpert, Pessac, France under the trade name EXPERTGEL®. Preferred poloxamers are synthetic copolymers of PEO and PPO represented by the following chemical structure (I):

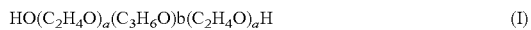
$$HO(C_2H_4O)_a(C_3H_6O)_b(C_2H_4O)_aH \quad (I)$$

These triblock polymers are modified at their termini by groups which can essentially be other chains of PEO-PPO-PEO, acid segments, amine groups, or PEOs. The chains are linked to the tripolymer chains via urethane bridges, urea bridges, allophanate bridges, and biuret bridges. In the above formula (I) a may range from about 100 or more to about 150 or less and b may range from about 40 or more to about 60 or less, in another embodiment a may range from about 101 or more to about 141 or less and b may range from about 44 or more to about 56 or less, and in a still further embodiment a is about 101 and b is about 56 or a is about 141 and b is about 44. The preferred average molecular weight of said triblock copolymer is from about 9840 to about 17400 Daltons. Preferably, the poloxamers comprise more than about 80% by weight of PEO-PPO-PEO. Commercially available water-soluble polymers are sold under the PLURONIC® trade name by BASF Corp. (Florham Park, N.J.). A preferred poloxamer is Poloxamer 338, wherein a is about 141 and b is about 44, having an average molecular weight of about 12700 to about 17400 Daltons. Another preferred poloxamer is Poloxamer 407, wherein a is about 101 and b is about 56, having an average molecular weight of about 9840 to about 14600 Daltons. Preferably, the poloxamers form urethane and/or urea bonds in the presence of water with the diisocyanate groups at the hydroxy moieties of the poloxamers. The poloxamers may be sold coupled with a copolymer of polypropyleneglycol-12 and saturated methylenediphenyldiisocyanate (poly[oxy-1,2-propanediyl]-α-hydro-ω-hydroxy-polymer with 1,1'-methylenebis[4-isocyanatocyclohexane]). Polypropyleneglycol-12 is hereinafter referred to as PPG-12. Saturated methylenediphenyldiisocyanate is hereinafter referred to as SMDI. These water-soluble polymers may be available from PolymerExpert, Pessac, France under the trade name EXPERTGEL®.

The water insoluble film forming polymer useful in the inventive sunscreen composition provides a synergistic effect with the water soluble polymer to retain SPF and PFA after exposure to adverse conditions such as water, in particular, salt water. Unexpectedly, the combination of the water soluble polymer and the water insoluble film forming polymer provides greater than 70% retention of at least one or both of SPF and PFA after exposure to water or salt water. Preferably, the combination provides greater than 85% of at least one or both of SPF and PFA after exposure to water or salt water. And more preferably, the combination provides greater than 90% of at least one or both of SPF and PFA after exposure to water or salt water.

The water insoluble film forming polymer includes acrylate copolymers, polyester copolymers, polyolefin copolymers, polyvinylpyrrolidone (PVP) copolymers, polyamide copolymers, polyurethane copolymers, or combinations thereof. Exemplary of acrylate copolymers may be styrene/acrylate copolymers such as DERMACRYL® E available from Akzo Nobel Surface Chemistry LLC, Chicago, Ill.; or acrylates/$C_{12}$-$C_{22}$ alkyl methacrylate copolymer such as SOLTEX® OPT available from The Dow Chemical Company, Midland, Mich. Exemplary of polyester copolymers may be polyester-7 (and) neopentyl glycol diheptanoate such as LEXFILM™ Sun available from Inolex Inc. of Philadelphia, Pa.; or polyglyceryl-3 stearate/isostearate/dimer dilinoleate such as COSMOSURF® PG available from Surfatech Corporation, Lawrenceville, Ga. Exemplary of polyolefin copolymers may be polyisobutene such as PERMETHYL® 284C available from Presperse, Inc., Somerset, N.J.; or polyethylene such as JEENATE® 3H available from Jeen International, Corporation, Fairfield, N.J. Exemplary of polyvinylpyrrolidone copolymers may be GANEX™ v-220 available from Ashland Inc., Covington, Ky. Exemplary of polyamide copolymers may be polyamide-8 such as OLEOCRAFT LP-20 available from Croda International Plc, East Yorkshire, United Kingdom. Exemplary of polyurethane copolymers may be polyurethane-34 such as BAYCUSAN® C1000 available from Bayer MaterialScience LLC, Pittsburgh, Pa.

Preferred water insoluble film forming polymers are acrylate copolymers, polyester copolymers, polyolefin copolymers, alone or in combination. These water insoluble film forming polymers allows the inventive sunscreen composition to retain greater than 70%, and preferably greater than 85%, of the in vitro SPF retention after immersion in water. Contrast this with a commercially available sunscreen product such as Banana Boat Sport SPF 50 Lotion sold by Energizer Personal Care, LLC, Shelton, Conn., which does not contain the synergistic polymer combination, and that only retains about a third of the in vitro SPF after immersion in water and less than 20% of the in vitro SPF after immersion in salt water following the conditions outlined in the 2011 FDA final monograph for water resistance.

Preferably, the water insoluble film forming polymer is present in an amount of about 0.01 wt. % to about 5 wt. %, and more preferably from about 1 wt. % to about 2 wt. % although unexpected benefits are seen at concentrations as low as about 0.5 wt. %. While the water insoluble film forming polymers are known film formers, it is interesting and unexpected that the addition of the water soluble polymer would provide a significant boost in water resistance to the final sunscreen composition.

In some embodiments of the present invention, the sunscreen composition includes sunscreen actives, and a synergistic combination of a water soluble polymer comprising about 1.5 wt. % Poloxamer 338 (and) (PPG-12)/SMDI copolymer and a water insoluble polymer comprising about 1.25 wt. % polyglyceryl-3 stearate/isostearate/dimer dilinoleate.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 0.5 wt. % of acrylates/$C_{12}$-$C_{22}$ alkyl methacrylate copolymer.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of acrylates/$C_{12}$-$C_{22}$ alkyl methacrylate copolymer.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 2 wt. % of acrylates/$C_{12}$-$C_{22}$ alkyl methacrylate copolymer.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of styrene/acrylates copolymer.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of vinylpyrrolidone/eicosene copolymer.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of polyamide-8.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of polyurethane-34.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of polydiethyleneglycol adipate/isophorone diisocyanate (IPDI).

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of polyester-7 (and) neopentyl glycol diheptanoate.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of polyisobutene.

In some embodiments of the present invention, the sunscreen composition includes sunscreen actives, and a synergistic combination of a water soluble polymer comprising about 1.5 wt. % of Poloxamer 338 (and) (PPG-12)/SMDI copolymer and a water insoluble film former comprising about 1.25 wt. % of polyethylene.

The sunscreen compositions of the present invention may optionally include other active or inactive ingredients such as those selected from, but not limited to, cosmetically acceptable carriers, oils, sterols, amino acids, moisturizers, powders, colorants (including pigments and/or dyes), pH adjusters, perfumes, essential oils, cosmetic active ingredients, vitamins, essential fatty acids, sphingolipids, self-tanning compounds such as dihydroxyacetone (DHA) and erythruloses, fillers, emulsifying agents, antioxidants, surfactants, additional film formers, chelating agents, gelling agents, thickeners, emollients, humectants, moisturizers, minerals, viscosity and/or rheology modifiers, keratolytics, retinoids, hormonal compounds, alpha-hydroxy acids, alpha-keto acids, anti-mycobacterial agents, anti-fungal agents, anti-microbials, anti-virals, analgesics, anti-allergenic agents, H1 or H2 antihistamines, anti-inflammatory agents, anti-irritants, anti-neoplastics, immune system boosting agents, immune system suppressing agents, anti-acne agents, anesthetics, antiseptics, insect repellents, skin cooling compounds, skin protectants, skin penetration enhancers, exfoliants, lubricants, fragrances, colorants, staining agents, depigmenting agents, hypopigmenting agents, preservatives, stabilizers, pharmaceutical agents, photostabilizing agents, spherical powders, one or more fragrances, plant extracts, absorbents, salicylic acid, alpha and beta hydroxy acids, vitamins including vitamins A, C, and E, retinol and its derivatives, or any mixtures thereof. The above is a list of examples and is not meant to be limiting.

The inventive sunscreen compositions of the present invention can be made using methods known to one of skill in the art of formulating skincare compositions. Multiple phases may be prepared prior to combining and homogenizing the resultant sunscreen composition. Preferably, the water soluble polymer is solubilized in water in an ice bath. An exemplary method of making the inventive sunscreen composition is to provide a pre-mix phase by adding the water soluble polymer to a quantity of water to form a clear solution with stirring in an ice bath. Other water soluble components may be added to this pre-mix and homogenized accordingly with heating to about 30° to 35° C. until uniform. To another vessel are added the non-aqueous-phase components including, preferably, the sunscreen actives and the water insoluble film former, with stirring and heating to about 70° to 75° C. until uniform. The non-aqueous phase components are added to the aqueous phase with mixing until homogenized. Preservatives such as phenoxyethanol may be added at this time. Then the batch is cooled to room temperature. Adjustments to the pH of the final composition can be made at this time.

In vitro SPF and critical wavelength ($\lambda_c$) data were obtained using a Labsphere Ultraviolet Transmittance Analyzer (Model UV-2000 available from the Solar Light Company, Philadelphia, Pa.) and presented in TABLE II. Samples of the sunscreen compositions weighing 1.6 mg/cm$^2$ were transferred by an adjustable pipette and uniformly applied to a Schonberg sand-blast PMMA plate (roughness 6 μm) by finger with a pre-saturated finger cot. After application, the coated plate was air dried for 15 minutes. The sample plate was then placed inside the Labsphere Analyzer. Irradiation took place at 4 randomly selected points. The readings were recorded by the analyzer and the calculation of the SPF value was based on the following equation:

$$SPF = \frac{\int_{280\ nm}^{400\ nm} E_\lambda \cdot S_\lambda \cdot d\lambda}{\int_{280\ nm}^{400\ nm} E_\lambda \cdot S_\lambda \cdot T_\lambda \cdot d\lambda}$$

with the use of built-in software: UV-2000 application Version 1.1.0.0, wherein $E_\lambda$ is defined as the Commission Internationale de l'Eclairage (CIE) erythemal spectral effectiveness, $S_\lambda$ is designated as the solar spectral irradiance, and $T_\lambda$ is the spectral transmittance of the sample as measured on the UV-2000. An average of four readings was recorded as the in-vitro SPF value of each sample shown in Table I.

Methodology set forth in 21 C.F.R. § 352.76 (2011 U.S. Food and Drug Administration Final Sunscreen Monograph) was used to demonstrate how the present invention, when applied onto human skin, forms a durable membrane which is strongly resistant to removal during bathing, swimming or sweating. This allows for the present invention to remain potent while being used either in or out of water, as well as before, during, and after periods of perspiration.

The following examples were prepared with 1.25 wt. % of the water soluble polymer Poloxamer 338 (and) (PPG-12)/SMDI copolymer, and a variety of water-insoluble film formers to show the synergistic effect of the water-soluble polymer and the water-insoluble polymer in retaining the SPF after the water resistance test and in vitro SPF and critical wavelength data determined accordingly. All samples contained the following representative sunscreen actives: 10 wt. % homosalate, 4 wt. % octocrylene, 5 wt. % octisalate, and 3 wt. % avobenzone. They are all formulated as lotions.

TABLE I

| Example | Water-insoluble Film Former (INCI names) | In vitro SPF | SPF after immersion in tap water | SPF retained |
|---|---|---|---|---|
| 1 | styrene/acrylate copolymer | 103 | 79 | 77% |
| 2 | acrylates/$C_{12-22}$ alkyl methacrylate copolymer | 105 | 93 | 89% |
| 3 | vinyl pyrrolidone/eicosene copolymer | 79 | 56 | 71% |
| 4 | polyamide-8 | 100 | 73 | 73% |
| 5 | polyurethane-34 | 93 | 73 | 78% |
| 6 | polydiethyleneglycol/adipate/IPDI | 72 | 59 | 82% |
| 7 | polyglyceryl-3 stearate/isostearate/ | 83 | 72 | 86% |
| 8 | polyester-7 (and) neopentyl glycol diheptanoate | 71 | 61 | 86% |
| 9 | polyisobutene | 72 | 66 | 92% |
| 10 | polyethylene | 65 | 50 | 77% |

Examples 1 to 10 show the unexpected synergistic effects of the water soluble polymer and the water-insoluble polymer in retaining greater than 70% of the SPF of the inventive sunscreen compositions after water immersion.

Examples 2, 11, and 12 contain varying amounts of the water-insoluble film former to which the SPF remains robust even after water immersion. There also appears to be a boosting effect depending on the amount of the water insoluble film former, which in these examples is the acrylates/$C_{12-22}$ alkyl methacrylate copolymer. The comparative sample, without the water soluble polymer, is commercially available BANANA BOAT® Sport SPF 50 Lotion made by Energizer Personal Care LLC, which contains 15.0 wt. % homosalate, 3.0 wt. % avobenzone, 5.0 wt. % octisalate, and 4.0 wt. % octocrylene.

TABLE II

| Example | Water-insoluble Film Former (INCI names) | Amount (wt. %) | In vitro SPF | SPF after immersion in tap water | SPF retained |
|---|---|---|---|---|---|
| BB SPF 50 | acrylates/$C_{12-22}$ alkyl methacrylate copolymer | 1.25 | 69 | 25 | 36% |
| 2 | acrylates/$C_{12-22}$ alkyl methacrylate copolymer | 1.25 | 105 | 93 | 89% |
| 11 | acrylates/$C_{12-22}$ alkyl methacrylate copolymer | 0.5 | 98 | 79 | 81% |
| 12 | acrylates/$C_{12-22}$ alkyl methacrylate copolymer | 2.0 | 107 | 97 | 91% |

All the inventive compositions had a critical wavelength of about 378 nm. Unexpectedly, the critical wavelength was completely retained after exposure to tap water.

The synergistic effects of the water soluble polymer and the water insoluble film former are even more pronounced after immersion in salt water (salinity of 4 wt. %) in comparison to the commercially available Banana Boat product as shown in Table III. Example 13 contained 10.0 wt. % homosalate, 3.0 wt. % avobenzone, 5.0 wt. % octisalate, and 4.0 wt. % octocrylene, with 1.25 wt. % of the water soluble polymer comprising Poloxamer 338 (and) (PPG-12)/SMDI copolymer. The SPF was determined on VITRO SKIN® testing substrates available from IMS Inc, Portland, Me., using the same product application methods as previous examples and as delineated above. After immersion in salt water, the inventive combination retained 88% of the original SPF showing a robustness not found in the commercial product that does not include the inventive combination.

TABLE III

| Example | Water-insoluble Film Former (INCI names) | Amount (wt. %) | VITRO SKIN SPF | SPF after immersion in salt water | SPF retained |
|---|---|---|---|---|---|
| BB SPF 50♦ | acrylates/$C_{12-22}$ alkyl methacrylate copolymer | 1.25 | 73 | 13 | 18% |
| 13 | acrylates/$C_{12-22}$ alkyl methacrylate copolymer | 1.25 | 56 | 49 | 88% |

The sunscreen compositions of the present invention are more robust after exposure to water and salt water providing consumers with lasting protection before and after water exposure than the commercially available sunscreen. SPF retention after salt water exposure provides an excellent indication that the inventive sunscreen compositions will stay on even during active exercise under sweaty conditions or at the beach. One of skill in the art will understand how to formulate the inventive sunscreen compositions into suitable consumer packaged products.

Further disclosed is a method of absorbing UV radiation on a keratinous substrate such as skin or hair, to limit or prevent damage from UV radiation is to apply a therapeutic amount of a sunscreen composition of the present invention to such keratinous substrate, and exposing the keratinous substrate to UV radiation.

While the present disclosure has been particularly described, in conjunction with specific preferred embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present disclosure.

What is claimed is:

1. A sunscreen composition comprising:
   a sunscreen active,
   a water soluble triblock polymer consisting of a central polypropylene oxide (PPO) block flanked on each side by polyethylene oxide (PEO) blocks, wherein said water soluble triblock polymer is in a mixture with polypropylene glycol-12/saturated methylene diphenyl diisocyanate copolymer, and wherein an average molecular weight of said water soluble triblock copolymer is 9840 Daltons to 17400 Daltons, and
   a water insoluble film forming polymer comprising:
      acrylate copolymers, wherein said acrylate copolymers include acrylates/C12-C22 alkyl methacrylate copolymer or styrene/acrylate copolymer,
      polyester copolymers, wherein said polyester copolymers include polydiethyleneglycol adipate/isophorone diisocyanate,
      polyolefin copolymers, wherein said polyolefin copolymers include polyisobutene or polyethylene,
      polyvinylpyrrolidone copolymers, wherein said polyvinylpyrrolidone copolymers include polyvinylpyrrolidone/eicosene copolymer,
      polyamide copolymers,
      polyurethane copolymers,
      or combinations thereof,
   wherein said water insoluble film forming polymer is present in an amount of about 0.1 wt. % to about 5.0 wt. % based on a total weight of the sunscreen composition.

2. The sunscreen composition of claim 1, wherein said sunscreen active comprises p-aminobenzoic acid, butyl methoxydibenzoylmethane, benzophenones, hydroxy-substituted benzophenones, methoxy-substituted benzophenones, benzophonone-1, benzophenone-2, benzophenone-3, benzophenone-4, benzophenone-6, benzophenone-8, benzophenone-12, methoxycinnamate, ethyl dihydroxypropyl-p-aminobenzoate, glyceryl-p-aminobenzoate, homosalate, methyl anthranilate, octocrylene, octyl dimethyl-p-aminobenzoate, octyl methoxycinnamate, octyl salicylate, 2 phenylbenzimidazole-5-sulphonic acid, triethanolamine salicylate, 3-(4-methylbenzylidene)-camphor, red petrolatum,3-(4-methylbenzyldine)boran-2-one (methylbenzindinecamphor), benzotriazole, salicylates, phenylbenzimidazole-5-sulfonic acid, methylene bis-benzotriazolyl tetramethylbutyl phenol, avobenzone, 4-isopropyldibenzoylmethane, butylmethoxydibenzoylmethane, octisalate, oxybenzone, bis-ethylhexyloxyphenol methoxy triazine, 4-isopropyl-dibenzoylmethane, metal oxides, zinc oxide, octyltriethoxy silanol, titanium dioxide, alumina, triethoxy silane, or combinations thereof.

3. The sunscreen composition of claim 1, wherein said sunscreen active is present in an amount of about 1.0 wt. % to about 40.0 wt. % based on a total weight of the sunscreen composition.

4. The sunscreen composition of claim 1, wherein said mixture is present in an amount of about 0.01 wt. % to about 20.0 wt. % based on a total weight of the sunscreen composition.

5. The sunscreen composition of claim 1, wherein said water insoluble film forming polymer is present in an amount of about 0.1 wt. % to about 2.5 wt. % based on a total weight of the sunscreen composition.

6. The sunscreen composition of claim 5, wherein said water insoluble film forming polymer is present in an amount of about 0.5 wt. % to about 2.0 wt. % based on a total weight of the sunscreen composition.

7. A sunscreen composition comprising:
   a sunscreen active,
   a water soluble triblock polymer consisting of a central polypropylene oxide (PPO) block flanked on each side by polyethylene oxide (PEO) blocks represented by the following structure:

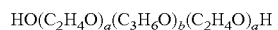

$$HO(C_2H_4O)_a(C_3H_6O)_b(C_2H_4O)_aH$$

wherein (a) and (b) represent the number of units of PEO blocks and PPO blocks, respectively, and wherein an average molecular weight of said water soluble triblock copolymer is 9840 Daltons to 17400 Daltons;
   polypropylene glycol-12/saturated methylene diphenyl diisocyanate copolymer; and
   a water insoluble film forming polymer selected from acrylates/C12-C22 alkyl methacrylate copolymer, styrene/acrylate copolymer, polydiethyleneglycol adipate/isophorone diisocyanate copolymer, polyisobutene, polyethylene, polyvinylpyrrolidone/eicosene copolymer, or combinations thereof, wherein said water insoluble film forming polymer is present in an amount of about 0.1 wt. % to about 5.0 wt. % based on a total weight of the sunscreen composition.

8. The sunscreen composition of claim 7, wherein said sunscreen active comprises p-aminobenzoic acid, butyl methoxydibenzoylmethane, benzophenones, hydroxy-substituted benzophenones, methoxy-substituted benzophenones, benzophonone-1, benzophenone-2, benzophenone-3, benzophenone-4, benzophenone-6, benzophenone-8, benzophenone-12, methoxycinnamate, ethyl dihydroxypropyl-p-aminobenzoate, glyceryl-p-aminobenzoate, homosalate, methyl anthranilate, octocrylene, octyl dimethyl-p-aminobenzoate, octyl methoxycinnamate, octyl salicylate, 2 phenylbenzimidazole-5-sulphonic acid, triethanolamine salicylate, 3-(4-methylbenzylidene)-camphor, red petrolatum,3-(4-methylbenzyldine)boran-2-one (methylbenzindinecamphor), benzotriazole, salicylates, phenylbenzimidazole-5-sulfonic acid, methylene bis-benzotriazolyl tetramethylbutyl phenol, avobenzone, 4-isopropyldibenzoylmethane, butylmethoxydibenzoylmethane, octisalate, oxybenzone, bis-ethylhexyloxyphenol methoxy triazine, 4-isopropyl-dibenzoylmethane, metal oxides, zinc oxide, octyltriethoxy silanol, titanium dioxide, alumina, triethoxy silane, or combinations thereof.

9. The sunscreen composition of claim 7, wherein said sunscreen active is present in an amount of about 1.0 wt. % to about 40.0 wt. % based on a total weight of the sunscreen composition.

10. The sunscreen composition of claim 7, wherein said water soluble triblock polymer is in a mixture with polypropylene glycol-12/saturated methylene diphenyl diisocyanate copolymer.

11. The sunscreen composition of claim 10, wherein said mixture is present in an amount of about 0.01 wt. % to about 20.0 wt. % based on a total weight of the sunscreen composition.

12. The sunscreen composition of claim 7, wherein said water insoluble film forming polymer is present in an amount of about 0.1 wt. % to about 2.5 wt. % based on a total weight of the sunscreen composition.

13. The sunscreen composition of claim 12, wherein said water insoluble film forming polymer is present in an amount of about 0.5 wt. % to about 2.0 wt. % based on a total weight of the sunscreen composition.

14. The sunscreen composition of claim 7, wherein said acrylates/C12-C22 alkyl methacrylate copolymer is present in an amount of about 0.5 wt. % to about 2.0 wt. % based on a total weight of the sunscreen composition.

15. The sunscreen composition of claim 7, wherein:
 (i) a is 100 to 150, and
  b is 40 to 60; or
 (ii) a is 101 to 141, and
  b is 44 to 56; or
 (iii) a is 101 and b is 56; or
 (iv) a is 141 and b is 44.

16. The sunscreen composition of claim 1, wherein said acrylates/C12-C22 alkyl methacrylate copolymer is present in an amount of about 0.5 wt. % to about 2.0 wt. % based on a total weight of the sunscreen composition.

* * * * *